United States Patent
Finch et al.

(10) Patent No.: US 7,872,224 B2
(45) Date of Patent: Jan. 18, 2011

(54) APPARATUS AND METHOD FOR POSITIONING A DISCHARGE TUBE WITH RESPECT TO AN ORIFICE

(75) Inventors: Jeffrey W. Finch, Gig Harbor, WA (US); Charles Murphy, Norton, MA (US)

(73) Assignee: Water Technologies Corporation, Milford, MA (US)

( * ) Notice: Subject to any disclaimer, the term of this patent is extended or adjusted under 35 U.S.C. 154(b) by 484 days.

(21) Appl. No.: 11/815,569

(22) PCT Filed: Feb. 6, 2006

(86) PCT No.: PCT/US2006/004037

§ 371 (c)(1),
(2), (4) Date: Jul. 21, 2008

(87) PCT Pub. No.: WO2006/086273

PCT Pub. Date: Aug. 17, 2006

(65) Prior Publication Data

US 2008/0277574 A1    Nov. 13, 2008

Related U.S. Application Data

(60) Provisional application No. 60/651,147, filed on Feb. 9, 2005.

(51) Int. Cl.
*H01J 49/26* (2006.01)
*B01D 59/44* (2006.01)

(52) U.S. Cl. .................. 250/288; 250/428; 250/281; 250/282

(58) Field of Classification Search ................. 250/281, 250/282, 288, 306, 307, 423 R, 424, 428, 250/440.11
See application file for complete search history.

(56) References Cited

U.S. PATENT DOCUMENTS

| | | | |
|---|---|---|---|
| 4,740,298 A * | 4/1988 | Andresen et al. | 210/198.3 |
| 4,740,872 A * | 4/1988 | Chou | 362/183 |
| 5,572,023 A | 11/1996 | Caprioli | |
| 6,207,954 B1 | 3/2001 | Andrien, Jr. et al. | |
| 6,337,480 B1 | 1/2002 | Andrien, Jr. et al. | |
| 6,458,597 B1 | 10/2002 | Andrien, Jr. et al. | |
| 6,541,767 B1 | 4/2003 | Kato | |
| 6,784,439 B2 | 8/2004 | Van Berkel | |
| 6,797,948 B1 * | 9/2004 | Wang | 250/292 |

(Continued)

OTHER PUBLICATIONS

Davis, Michael T.; Micro Electrospray Interface Design And Method Selection For Tandem MS Analyses Of Complex Peptide Mixtures; Micro Electrospray Mass Spectrometry, p. 1 of 19 (http://www.abrf.org/ABRFNews/1997September1997/sep97microesms.html.

(Continued)

*Primary Examiner*—Bernard E Souw
(74) *Attorney, Agent, or Firm*—Anthony J. Janiuk; Jamie H. Rose (57) ABSTRACT

Embodiments of the present invention facilitate servicing or changing a discharge tube or modifying the position of a discharge tube with respect to a orifice of a detector and/or a nebulizing gas conduit. The apparatus features a discharge tube housing that slidably receives a discharge tube. A union coupling the discharge tube to a source of fluid is slidably mounted to a mounting assembly holding the tube housing.

56 Claims, 3 Drawing Sheets

U.S. PATENT DOCUMENTS

| | | | |
|---|---|---|---|
| 6,831,274 B2 | 12/2004 | Smith et al. | |
| 6,835,929 B2* | 12/2004 | Finch | 250/288 |
| 2003/0234368 A1* | 12/2003 | Finch | 250/423 P |
| 2004/0256550 A1* | 12/2004 | Finch | 250/288 |
| 2007/0221839 A1* | 9/2007 | Goodley et al. | 250/288 |

OTHER PUBLICATIONS

Abian, J.; Comparison of Conventional, Narrow-bore and Capillary Liquid Chromatography/Mass Spectrometry for Electrospray Ionization Mass Spectrometry: Practical Considerations, Journal of Mass Spectrometry 34, 244-254 (1999); Special Feature: Tutorial.

* cited by examiner

APPARATUS AND METHOD FOR POSITIONING A DISCHARGE TUBE WITH RESPECT TO AN ORIFICE

CROSS REFERENCE TO RELATED APPLICATIONS AND PATENTS

This application is the National Stage of International Application No. PCT/US2006/004037, filed on Feb. 6, 2006, which claims priority from U.S. Provisional Patent Application No. 60/651,147 filed on Feb. 9, 2005. The entire contents of these applications are incorporated herein by reference.

FIELD OF INVENTION

This invention relates to equipment and instrumentation in which it is desirable to position a discharge tube with respect to an orifice.

BACKGROUND OF THE INVENTION

Embodiments of the present invention have application where it is desired to discharge fluids into an orifice for further processing. As capillaries, tubes, conduits and pipes for discharging fluid become smaller, such capillaries, tubes, conduits and pipes become more difficult to handle and to position with respect to orifices with which the discharge capillary, tube, conduit or pipe needs to communicate. This discussion will use the terms "capillary", "tube", "conduit" and "pipe" synonymously and without connoting differences in size or scale.

Embodiments of the present invention have particular application in instruments in which one device needs to be placed in fluid communication with another. For example, without limitation, in chemical analysis, it is useful to have one instrument, a chromatographic system, placed in communication with a detector. A chromatographic system is a instrument or combination of instruments that perform chemical separations.

A chromatographic separation is the separation of compounds from each other based on the different affinity the compounds have to an immobile phase. Solutions carrying the compounds move through the immobile phase causing the compounds to separate. High performance liquid chromatography is performed with a liquid as the mobile phase. The liquid is forced through a immobile solid phase comprising a bed of particles or matrix or monolithic porous structures or the walls of vessels in which the mobile phase flows.

The detector may take different forms. Common detectors include optical sensors, mass sensors and electron spin detectors and the like. One form of mass detector is a mass spectrometer. Mass spectrometers operate under vacuum.

The term "chromatographic system" is used herein to describe equipment to perform chemical separations. These systems move fluids under pressure. Chromatographic systems are placed in fluid communication with mass spectrometers through interfaces. These interfaces create or maintain the compounds in an ionic form and place a stream of fluid containing the ions into an atmosphere where the stream is vaporized and the ions are received in an orifice of the mass spectrometer. The orifice separates the low pressure chambers of the mass spectrometer from the atmospheric pressure of the interface.

The stream of fluid containing the ions is created by small diameter conduits, tubes or capillaries. These conduits, tubes and capillaries are positioned with respect to the orifice to maximize signal and produce reproducible results. However, the tubes, conduits and capillaries can be occluded, or break or require changes for servicing or changes of methods. These tubes, capillaries and conduits are difficult to handle, align and fix in place.

SUMMARY OF THE INVENTION

Embodiments of the present invention feature apparatus with features which facilitate assembly and methods for assembling a discharge tube for alignment with an orifice. The discharge tube is useful for producing a stream of fluid of which a portion is received in an orifice of a down stream instrument or device.

One embodiment of the present invention, featuring an apparatus, is for holding a discharge tube having a distal end for receiving fluid and a proximal end for discharging fluid. The discharged fluid is to be received in an orifice of a detector downstream from the discharge tube. The discharge tube has at least one wall defining an external surface and at least one wall defining an internal surface. The apparatus has a tube housing for mounting at or about the orifice of a detector. The tube housing has at least one exterior surface and at least one internal wall. The internal wall defines a chamber having a proximal opening for positioning about the orifice of a detector and a distal opening away for the orifice of a detector. The chamber is constructed and arranged to receive a discharge tube in the distal opening and projecting from said proximal opening. The chamber is in communication with source of a carrier gas. The carrier gas is conveyed to the proximal opening of the chamber between the external wall of the discharge tube and the internal wall of the chamber. The chamber has a wide section at the distal opening, and a narrow section towards the proximal opening, and a conical section. The conical section is interposed between the narrow section and the wide section. Tube securing means is affixed to the wide section and the conical section of the tube housing. Tube securing means engages the discharge tube in one of two modes; a release mode and a securing mode. In the release mode the discharge tube is slideably engaged to allow the discharge tube to be moved within the chamber in a selected position with respect to the proximal opening of the tube housing. In the securing mode the discharge tube is fixed. Tube securing means has sealing means for substantially closing the distal opening with the discharge tube to the carrier gas when the tube securing means is in the securing mode. At least one of the tube housing and the tube securing means is capable of securing the tube housing at or about the orifice of the detector to facilitate the alignment of the discharge tube with the orifice of the detector.

Embodiments of the present invention allow the positioning of the discharge tube within a tube housing. The discharge tube is preferably received at the proximal opening of the tube housing to protect discharge opening. The tube housing with the discharge tube fitted to the chamber can mounted to the mass spectrometer in an aligned position with respect to the orifice. The tube housing can be sized to facilitate handling.

A preferred tube securing means comprises at least one ferrule or ferrule assembly comprising a ferrule and ferrule sleeve. Such ferrule has a ferrule opening for receiving the discharge tube and a conical shape for cooperating with the conical section of the chamber. The ferrule is received in the conical section of the chamber with the discharge tube in the ferrule opening to sealing engage the conical section of the chamber and the exterior surface of the discharge tube upon compression. Thus, the ferrule prevents the carrier gas from exiting the chamber at the distal opening and fixes the position of the discharge tube. A ferrule sleeve is used to accommodate a discharge tube in which the exterior diameter does not correspond to the internal diameter of the ferrule opening.

A preferred tube securing means further comprises ferrule compression means. Ferrule compression means may assume several forms including, by way of example without limitation, screw, cams and nuts. One preferred embodiment of ferrule compression means is a ferrule screw having threads. The chamber at the wide opening has threads for receiving the ferrule screw to allow the ferrule screw to be secured and tightened against the ferrule. A preferred ferrule screw has at least one handle or ratchet means for facilitating turning of the screw.

Preferably, the tube housing has a projecting conduit and the chamber extends through the projecting conduit ending at the proximal opening. The projecting conduit is preferably electro-conductive to place a charge upon one or more droplets discharged from a discharge tube and/or to direct droplets bearing a charge towards the orifice.

Embodiments of the present invention can receive different discharge tubes having different external diameters with a simple change in ferrule or ferrule sleeve and a simple change in the projecting conduit.

Preferably, the apparatus further comprises a union assembly for receiving the distal end of the discharge tube and placing the discharge tube in communication with a source of fluid. A preferred source of fluid is a capillary, and most preferred, a fused silica capillary. A preferred union assembly has a union housing. The union housing has a union chamber for receiving the capillary and the discharge tube.

Preferably, the union assembly further comprises capillary securing means and discharge tube securing means. A preferred capillary securing means comprises at least one capillary ferrule and one capillary screw element. The capillary screw element has a capillary opening for receiving the capillary. The capillary ferrule sealing engages the capillary and the union housing upon compression.

A preferred discharge tube securing means comprises at least one tube ferrule and one tube screw element. The tube screw element has a tube opening for receiving the discharge tube. The tube ferrule sealing engages the discharge tube and the union housing upon compression. Thus, different capillaries and discharge tubes can be used. These capillaries and discharge tubes can have different external diameters. The differences in external diameters can be addressed with a simple change in ferrule with a matching diameter.

Preferably, the union housing is electro-conductive to place a charge on ions in solution flowing through the union chamber. Preferably, the discharge tube and the capillary are places in abutting relationship that brings the fluid in contact with the union housing.

Preferably, the apparatus further comprises a mounting assembly. The mounting assembly holds the tube housing in position with respect to the orifice of the detector and fixes the union assembly in position with respect to the tube housing. A preferred mounting assembly comprises a union holder, with union affixing means for detaching and affixing said union assembly. A preferred union holder has a body having a channel for receiving the union housing. The union holder is preferably secured with a union screw.

A preferred mounting assembly has slide means for slidably positioning the union holder with respect to the tube housing. One preferred mounting assembly comprises a plate having slide means. For example, the plate and the union holder have cooperating sliding track and carriage means. The sliding track preferably comprises one or more grooves and at least one of the grooves has one or more retaining ridges. Preferably, the carriage means comprises a carriage section of the union holder. The carriage section has one or more keyed edges, which keyed edges are retained in said groove by the retaining ridge. Other slide means include folding arms and telescoping sections.

Preferably, the apparatus further comprises locking means to fix the position of said union holder with respect to said tube housing. One preferred locking means is a locking screw and a locking screw opening. The locking screw opening is in the union holder. The locking screw and locking screw opening having cooperating threads. The locking screw has a release position in which the union holder slides in one or more grooves and a locked position in which the union holder is unable to move, to fix the union holder in position.

The apparatus of the present invention may comprise any or chromatography system or detector and is particularly well suited as part of a mass spectrometer.

One further embodiment of the present invention is directed to a method of making a fluid discharge apparatus. The method comprises the steps of providing an apparatus, for holding a discharge tube having a distal end for receiving fluid and a proximal end for discharging fluid, which discharged fluid is to be received in an orifice of a detector. The discharge tube has at least one wall defining an external surface and at least one wall defining an internal surface. The apparatus has a tube housing for mounting at or about an orifice of a detector. The tube housing has at least one exterior surface and at least one internal wall defining a chamber having a proximal opening for positioning about said orifice of a detector and a distal opening away for said orifice of a detector. The chamber is constructed and arranged to receive a discharge tube extending from the distal opening and projecting from said proximal opening. The chamber is in communication with source of a carrier gas, with the carrier gas conveyed to the proximal opening of the chamber between the external wall of the discharge tube and the internal wall of the chamber. The chamber has a wide section at the distal opening, and a narrow section towards the proximal opening, and a conical section. The conical section is interposed between said narrow section and said wide section and facilitates the insertion of the discharge tube, guiding the discharge tube into the narrow section. The apparatus further comprises tube securing means and sealing means affixed to the wide section and conical section of the tube housing and engaging the discharge tube in a release mode and a securing mode. In the release mode, the discharge tube is slideably engaged to allow the discharge tube to be moved within the chamber in a selected position with respect to the proximal opening of the tube housing. In the securing mode, the discharge tube is fixed, with the sealing means substantially closing the distal opening with the discharge tube to the carrier gas. At least one of the tube housing and the tube securing means is capable of securing the tube housing at or about said orifice of the detector to facilitate the alignment of the discharge tube with the orifice of the detector. The method further comprises the step of inserting a discharge tube in the distal opening of the tube housing through the chamber and projecting from the proximal opening. And, securing the discharge tube with securing means to affix the discharge tube and seal the distal opening.

A preferred tube securing means comprises at least one ferrule, or ferrule and ferrule sleeve, and the method further comprising the step of fitting said ferrule to said discharge tube. Preferably, tube securing means comprises ferrule compression means and said method further comprises the step of compressing said ferrule with ferrule compression means. A preferred ferrule compression means comprises a screw having threads and said chamber at said wide opening has threads for receiving said screw. The method thus comprises the step fitting said screw to the discharge tube, and securing and tightening the screw against the ferrule. Preferably, the screw has at least one handle means for facilitating turning of the screw. In the alternative, compression means may use cams and one or more levers and the method comprises the step of moving the lever or levers.

Preferably, the apparatus further comprising a union assembly for receiving the distal end of the discharge tube and placing the discharge tube in communication with a source of fluid. And, the method comprising the step of placing the distal end of the discharge tube in communication with the union assembly.

A preferred source of fluid is a capillary and, most preferred, a fused silica capillary. And, preferably, union assembly comprises a union housing having a union chamber for receiving the capillary and said discharge tube. The method, preferably, comprises the step of fitting the discharge tube and the capillary in the union housing.

Preferably, the union assembly further comprises capillary securing means and discharge tube securing means. And, the method comprises the step of securing the discharge tube and the capillary fitted in said union housing with the securing means. A preferred securing means comprises at least one capillary ferrule, capillary screw element, discharge tube ferrule and discharge screw element.

Preferably, the apparatus further comprises a mounting assembly. The mounting assembly holds the tube housing in position with respect to the orifice of the instrument or detector and holds the union assembly in position with respect to the tube housing. And, preferably, the mounting assembly comprises a union holder having union affixing means for detaching and affixing said union assembly. The method preferably comprises the step of affixing the union assembly to the mounting assembly.

Preferably, the mounting assembly has slide means for slidably positioning the union holder with respect to the tube housing. A preferred method comprises the step of sliding the union holder in position with respect to the tube housing with said discharge tube abutting said fused capillary.

Preferably, the apparatus further comprises locking means to fix the position of the union holder with respect to said tube housing. And, the method further comprises the step of using locking means to fix the position of said union holder.

Embodiments of the present invention have particular utility with respect to mass spectrometer instruments to facilitate changing, servicing and adjusting discharge tubes for discharging fluids towards an orifice of a low pressure chamber.

These and other features and advantages will be apparent to those skilled in the art upon viewing the figures and reading the detailed description that follows.

DETAILED DESCRIPTION OF THE INVENTION

Embodiments of the present invention will be described in detail as an apparatus an apparatus, for holding a discharge tube having a distal end for receiving fluid and a proximal end for discharging fluid, which discharged fluid is to be received in an orifice of a detector. The apparatus and method have particular utility with respect to mass spectrometry and high pressure liquid chromatograph interfaces. As used herein "high pressure liquid chromatography" means chemical separations under pressures greater than one atmosphere. Those skilled in the art will readily recognize that embodiments of the present invention have broad application which include any use of discharge tube that communicate with other instruments and equipment through orifices.

Figure 1:
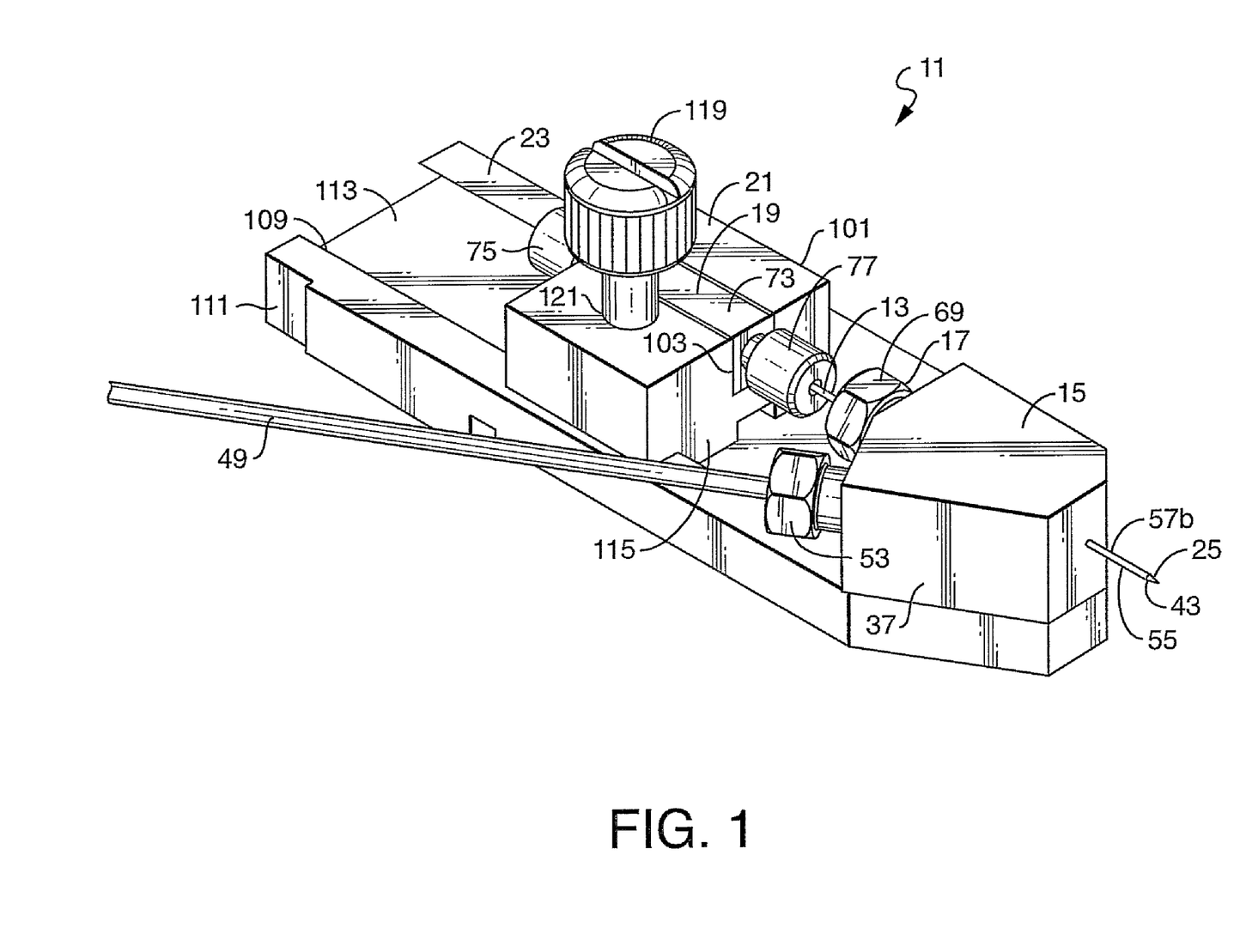
FIG. 1 depicts a slightly elevated side-front view of an apparatus having features of the present invention.

Turning now to FIG. 1, an apparatus embodying feature of the present invention, generally designated by the numeral 11, is depicted. The apparatus 11 is for making a fluid stream [not shown] comprising ions and vapor in a position to be received through an orifice [not shown] of a mass spectrometer [not shown]. The orifice is in the exterior wall separating relatively high pressure areas of the mass spectrometer from a lower pressure area. Mass spectrometers and orifices in mass spectrometer are known in the art.

Figure 2:
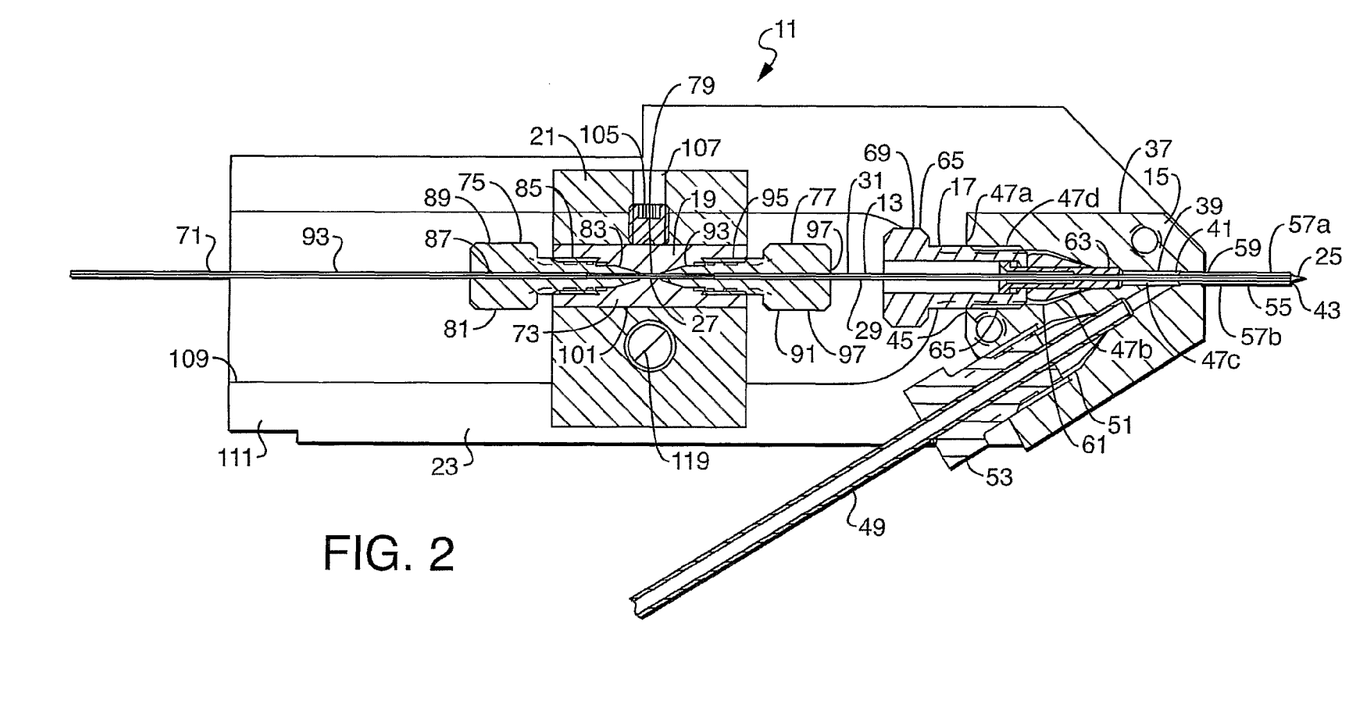
FIG. 2 depicts a top cross sectional view of the apparatus of FIG. 1.

Apparatus 11 has the following major elements: a discharge tube 13, a tube housing 15, tube securing means 17, a union assembly 19, union holder 21 and a mounting assembly 23. Turning now to FIG. 2, the discharge tube 13 has a proximal end 25 for placement towards an orifice to discharge fluid, and a distal end 27 for receiving fluid. The proximal end 25 is preferably drawn to a fine point. The fine point is delicate and great effort is normally taken to avoid breaking the point. The discharge tube 13 has at least one external wall 29 defining an external surface and at least one interior wall 31 defining an internal surface. Fluid is received at the distal end 27 within the interior wall 31 and passes through the discharge tube 13 and out the proximal end 25.

Discharge tube 13 is made from a drawn fused silica capillary, stainless steel or other metals. The discharge tube 13, if made from a fused silica material, for some applications, may be coated with a electro-conductive material [not shown] in a manner known in the art. Individuals skilled in the art will recognize that operation of liquid chromatography systems and coupled to mass spectrometer may require discharge tubes 13 of different sizes. Discharge tube 13 has an outer diameter of approximately 40 microns to 500 microns. Discharge tube 13 has a typical inner diameter of approximately 5 microns to 30 microns. The discharge tube 13 has a length that may vary from 3 to 10 centimeters. Discharge tubes 13 are available from several venders under a variety of trademarks including NanoLC™, PicoTip™, PicoFrit™, POLYMICRO™ (Polymicro, Phoenix, Ariz., U.S.A.), Proxen Biosystems, (Odense, Denmark), GL Sciences, Inc. (Tokyo, Japan) and others. Discharge tubes 13 can become occluded, break or require service.

Returning now to FIG. 1, the proximal end 25 of the discharge tube 13 is aligned with the orifice [not shown] that is to receive fluid. The proximal end 25 of discharge tube cooperate with features of the tube housing 15 as will be discussed later. Thus, individuals fit a discharge tube 13 such that the fluid discharged from the proximal end 25 enters an orifice of a mass spectrometer. It is also desirable to have the distal end 27 communicate with a source of fluid with minimal dead volume. However, these objects are difficult to achieve due to the small size of the discharge tube 13 and the small volumes of fluid which are to be discharged.

Tube housing 15 is constructed and arranged for mounting at or about the orifice of a detector such as a mass spectrometer [not shown]. Tube housing 15 has at least one exterior surface 37 and at least one internal wall 39. Internal wall 39 defines a chamber 41 having a proximal opening 43 for positioning about the orifice [not shown] of a detector. Tube housing 15 has a distal opening 45 away for the orifice of a detector. The chamber 39 is constructed and arranged to receive the discharge tube 13. The discharge tube 13 is fitted with a portion projecting from the distal opening 45 and the tip projecting from the proximal opening 43.

Chamber 41 has a wide section 47a at the distal opening 45, and a narrow section 47c towards the proximal opening, and a conical section 47b. The conical section 47b is interposed between the narrow section 47c and the wide section. The chamber has a sleeve section 47d for receiving a tube sleeve.

Chamber 41 is in communication with source of a carrier or nebulizing gas [not shown] via a gas conduit 49. Gas conduit 49 is secured to the tube housing 15 by suitable means such a the gas ferrule 51 and gas screw 53. The nebulizing or carrier gas is conveyed to the proximal opening 43 of the chamber 41 between the external wall 29 of the discharge tube 13 and the internal wall 31 defining chamber 41. The gas conduit 49, gas ferrule 51, and gas screw 53 may be made of any machinable metal, or moldable or machinable plastic.

Tube housing 15 is made of any machinable metal or moldable or machinable plastic. A preferred metal is stainless steel. A preferred plastic is poly ethylene ethylene ketone (PEEK). Tube housing 15 has dimensions to cooperate with the discharge tube 13 with which it will be used. Tube housing is approximately two to five centimeters long at its greatest dimension. The chamber 41, at the narrow section 47c, has a diameter greater than the discharge tube 13 to allow the flow of nebulizing gas.

Tube housing 15 has a projecting conduit 55 formed as an integral part of the housing or, as depicted, a separate element. The projecting conduit 55 forms part of chamber 41 at the proximal opening 43. The projecting conduit 55 preferably forms the narrow section of the chamber 41 or part of the narrow section 43. As depicted, projecting conduit 55 has an inner wall 57a forming part of the chamber 41 and an outer diameter 57b. The tube housing 15 has a projecting conduit hole 59 in which the projecting conduit 55 fits. Preferably, the projecting conduit 55 is electro-conductive to place a charge upon one or more droplets discharged from the discharge tube 13 and/or to direct the droplets bearing a charge towards the orifice [not shown]. The projecting conduit 55 is preferably made of metal, such as stainless steel or plastic having an electro-conductive coating.

Tube securing means 17 is affixed to the wide section 47a and conical section 47b of chamber 41 of the tube housing 15. Tube securing means 17 engages the discharge tube 13 in a release mode and a securing mode. In the release mode, the discharge tube 13 is slideably engaged to allow the discharge tube 13 to be moved within the chamber 41. The discharge tube 13 is slid into a position in which the proximal end 27 is aligned with the proximal opening 43 of the tube housing 15 or the orifice [not shown]. In a selected position with respect to said proximal opening 43 of the tube housing 15. In the securing mode, the discharge tube 13 is fixed. That is, further sliding motion within chamber 41 is arrested.

Tube securing means 17 has sealing means in the form of a tube ferrule 61 for substantially closing the distal opening 45 with the discharge tube 13 to said carrier gas when the tube securing means 17 is in the securing mode. The tube ferrule 61 has a ferrule opening for receiving the discharge tube 13 and a conical shape for cooperating with the conical section 47b of chamber 41. The tube ferrule 61 is received in the conical section 47b with the discharge tube 13 in the ferrule opening to sealing engage the conical section 47b of the chamber 41 and the exterior surface 29 of the discharge tube 13 upon compression. Sealing engagement prevents the carrier gas from exiting the chamber 41 at the distal opening 27 and fixes the position of the discharge tube 13.

A sizing sleeve 63 is used to allow a single tube ferrule 61 to accommodate different discharge tubes 13. Sizing sleeve 63 slidably receives the discharge tube 13 in an axial opening. Tube ferrule 61 fits over the sizing sleeve 35 and the discharge tube 13.

Preferably, at least one of the tube ferrule 61 or tube housing 15 is comprised of a compressible material. A preferred compressible material is selected from the group consisting of deformable metals, polymers and plastics and solid agglomerated forms. A used herein the "agglomerated forms" refers to packing material and sealers which form a substantially cohesive mass, particularly, upon compression. One embodiment of tube ferrule 61 is made of a conductive material to place a change on a discharge tube 13 which discharge tube 13 is made of a conductive material or having a conductive coating. An electrical contact with a voltage source is effected with such tube ferrule 61. Such voltage source can comprise tube housing 15 if such housing is made of a conductive material.

Tube securing means 17 further comprises tube ferrule compression means in the form of a tube ferrule screw 65. Tube ferrule screw 65 and chamber 41 have cooperating threads 67. The threads 67 of the chamber 41 are at the wide section 47a. As tube ferrule screw 65 is turned, the tube ferrule screw 65 compresses the tube ferrule 61 to secure and seal the tube ferrule 61 against the conical section 47b of the chamber 41 and the discharge tube 13.

The tube ferrule screw 65 has at least one handle means for facilitating turning. For example, as depicted, tube ferrule screw 65 has a nut surface 69 to cooperate with a wrench held by a user. The nut surface 69 may also be fitted with a ratcheting mechanism [not shown] known in the art or wings [not shown] of the type commonly associated with wing nuts, or cams or other levers.

At least one of the tube housing 15 and the tube securing means 17 is capable of securing the tube housing 15 at or about the orifice of the detector. The tube housing 15 facilitates handling of the discharge tube 13 and the alignment of the discharge tube 13 with the orifice of the detector. As best seen in FIGS. 1 and 2, tube housing 15 is secured to mounting assembly 23 which in turn is affixed to a detector in a position aligned with the orifice.

Apparatus 11 further has a union assembly 19 for receiving the distal end 27 of the discharge tube 13 and placing the discharge tube 13 in communication with a source of fluid. As depicted in FIG. 2, this source of fluid is a fused silica capillary 71. However, those skilled in the art will readily recognize that the source of fluid may originate from many sources including by way of example, without limitation, columns, conduits, and other instruments.

Figure 3:
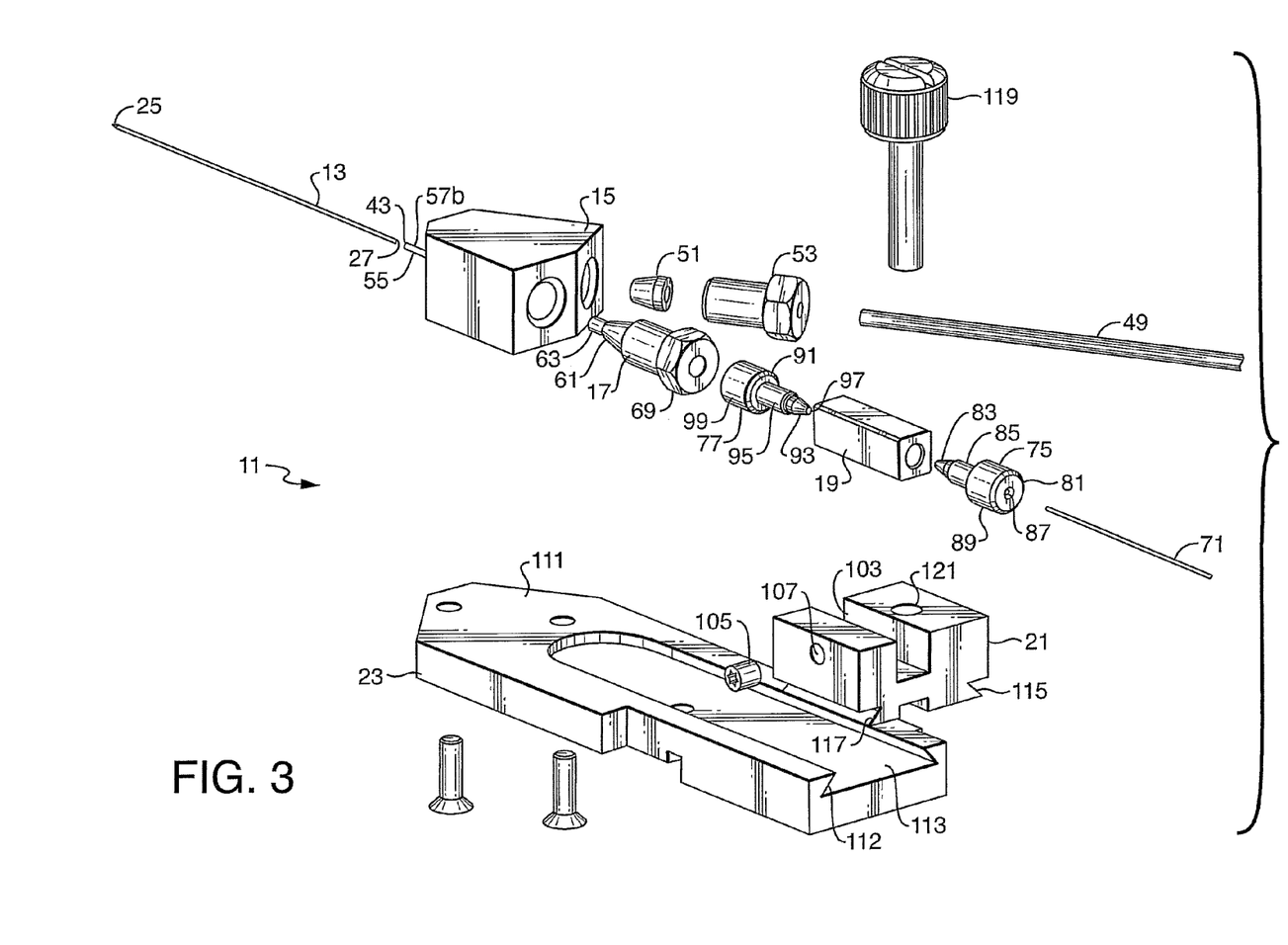
FIG. 3 depicts an exploded slightly elevated rear side view the apparatus of FIG. 1.

Turning now to FIGS. 2 and 3, union assembly 19 comprises a union housing 73, capillary securing means 75 and discharge tube securing means 77. The union housing has a union chamber 79 for receiving the fused silica capillary 71 and the discharge tube 13. A stop [not shown] can be built into union chamber 79 for centering fused silica capillary 71 and discharge tube 13. In the alternative, a stop plug [not shown] used in place of capillary securing means 75 can be used to center the fused silica capillary and discharge tube 13.

As depicted, the capillary securing means 75 comprises at least one capillary ferrule means in the form of a capillary ferrule screw 81. Capillary ferrule screw 81 is a unitary screw with features of a ferrule. It has an axial passage 87 through which a fused silica capillary is fitted. Capillary screw ferrule 81 has a conical section 83 which acts as a ferrule upon compression and a screw section 85 having threads that cooperate with threads in the union chamber 79. Upon tightening, the screw section 85 compresses the conical section 83 in sealing engagement. Other capillary securing means include, by way of example, without limitation, separate ferrules and screw elements [not shown] of the type previously described with respect to the tube securing means 17, or a packing or seals with compression sleeves or screw elements [not shown].

Preferably, capillary ferrule screw 81 has at least one handle means for facilitating turning. For example, as depicted, capillary ferrule screw 81 has a knurled surface 89 to facilitate tightening by hand. However, other surfaces can be readily substituted, such as a nut surface [not shown], a ratcheting mechanism [not shown] known in the art, or wings [not shown] of the type commonly associated with wing nuts, or cams or other levers.

Similarly, the discharge tube securing means 75 comprises at least one tube ferrule means in the form of tube ferrule screw 91. Tube ferrule screw 91 is a unitary screw with features of a ferrule. It has an axial passage 97 through which a discharge tube is fitted. tube screw ferrule 91 has a conical section 93 which acts as a ferrule upon compression and a screw section 95 having threads that cooperate with threads in the union chamber 79. Upon tightening, the screw section 95 compresses the conical section 93 in sealing engagement. Other discharge tube securing means 75 include, by way of example, without limitation, separate ferrules and screw elements [not shown] of the type previously described with respect to the tube securing means 17, or a packing or seals with compression sleeves or screw elements [not shown].

Preferably, tube ferrule screw 91 has at least one handle means for facilitating turning. For example, as depicted, tube ferrule screw 81 has a knurled surface 99 to facilitate tightening by hand. However, other surfaces can be readily substituted, such as a nut surface [not shown], a ratcheting mechanism [not shown] known in the art, or wings [not shown] of the type commonly associated with wing nuts, or cams or other levers. and one tube screw element, said tube screw element having a tube opening for receiving said discharge tube and said tube ferrule sealing engages said discharge tube and said union housing upon compression.

Preferably, at least one of the tube ferrule screw 91 or capillary ferrule screw 81 is made of a compressible material. A preferred compressible material is selected from the group consisting of deformable metals, polymers and plastics and solid agglomerated forms.

Preferably, the union housing 73 is electro-conductive to place a charge on ions in solution flowing through said union chamber 79. Fused silica capillary 71 has a capillary end 93 which is butted against the distal end 27 of discharge tube 13. Fluid flows through the fused capillary 71 and into the discharge tube 13. However, some fluid escapes and occupies the union chamber 79 providing electrical communication between the union housing and the fluids conveyed in the fused silica capillary 71 and discharge tube 13.

Union holder 21 has union affixing means for detaching and affixing the union assembly 19. Union holder 21 has a body 101 having a channel 103 for receiving the union housing 19. Turning now to FIG. 2, union securing screw 105 fits in a hole 107 in the body 101 of union holder 21. The union securing screw 105 and the hole 107 have cooperating threads to allow the union housing 73 to be received in the channel 103, slidably positioned to allow operation of the tube ferrule screw 91 and capillary ferrule screw 81, and fixed by tightening. However, those skilled in the art will recognize that union securing screw 105 can be replaced with other securing means such as clips, clamps, pins and the like.

The union holder 21 is secured to the mounting assembly 23. The mounting assembly 23 has slide means in the form of a sliding track 109 for slidably positioning the union holder 21 with respect to the tube housing 15 to accommodate discharge tubes 13 of different length.

As best seen in FIGS. 1 and 3, mounting assembly 23 comprises a plate 111 having grooves 113 forming the sliding track 109. The union holder 21 has carriage means in the form of a carriage section 115 with cooperating keyed edges 117 held in the grooves 113 of sliding track 109.

Individuals skilled in the art will recognize that the sliding means may take several forms. Other examples of sliding means include, without limitation, telescoping sections, folding linkages, and the like. As depicted, the plate 111 is made of a metal such as stainless steel or a plastic such as PEEK. Preferably, the plate 111 is made of an electro-conductive material to ground the major elements of the apparatus 11.

Locking means in the form of locking screw 119 fitted into a cooperating locking screw opening 121 fixes the position of said union holder 21 with respect to the tube housing 15. Other locking means include, by way of example, without limitation, clips, pins, clamps, and other suitable means. The locking screw 119 has a release position in which the union holder 21 slides in one or more grooves and a locked position in which the union holder 21 is unable to move to fix the union holder 21 in position.

The apparatus 11 is preferably incorporated into a detector such as a mass spectrometer. The discharge tube 13 discharge or emits fluid towards an orifice of the low pressure housing of the mass spectrometer.

Embodiments of the present invention, directed to a method of making and using the fluid discharge apparatus 11, are exemplified in the following discussion. The method of making a fluid discharge apparatus comprising the steps providing an apparatus 11, for holding a discharge tube 13. The apparatus 11 has a tube housing 15 for mounting at or about an orifice of a detector [not shown]. The tube housing 15 has at least one exterior surface 37 and at least one internal wall 39. The interior wall 39 defines a chamber 41 having a proximal opening 43. The chamber 41 is constructed and arranged to receive a discharge tube 13 projecting from the proximal opening 43.

The method comprises the step of inserting a discharge tube 13 into the chamber 41 and projecting from the proximal opening 43. The discharge tube 13 is affixed to the tube housing 15 via tube securing means 17 which allows discharge tube 13 to be moved within the chamber 41 into a selected position with respect to the proximal opening 43 of the tube housing 15. In the selected position, the discharge tube 13 is secured in position. And, the distal opening 45 with the discharge tube 13 protruding therefrom is closed to the carrier gas.

Preferably, the apparatus 11 further comprises a union assembly 19 for receiving the distal end 27 of the discharge tube 13 and placing the discharge tube 13 in communication with a source of fluid. The method further comprises the step of placing the distal end 27 of the discharge tube 13 in communication with the union assembly 19.

A preferred source of fluid is a fused silica capillary 71. The method further comprises the step of coupling the fused silica capillary 71 to the union assembly 19.

Preferably, the union assembly is received in a union holder 21, which union holder 21 is slidably mounted to a mounting assembly 23 to which the tube holder 15 is mounted. A positioning stop can be used to center the digital end 27 of discharge tube 13 in union holder 21. The union holder 21 is moved along sliding track 109 to position the proximal end 25 of discharge tube 13 in proper alignment with the orifice of the detector, or to bring the fused silica capillary 71 in abutting relationship with the distal end 27 of the discharge tube 13. In the proper position, the locking screw 119 is tightened and capillary ferrule screw 81, discharge tube ferrule 61 and tube ferrule screw 69 tightened.

Embodiments of the present invention facilitate servicing or changing a discharge tube 13 or modifying the position of a discharge tube 13 with respect to a orifice of a detector and/or a nebulizing gas conduit.

Thus, the present invention has been describe with respect to the preferred embodiments which are subject to alteration and modification. Therefore, the present invention should not be limited to the precise details but should encompass the subject matter of the following claims and their equivalents.

We claim:

1. An apparatus, for holding a discharge tube having a distal end for receiving fluid and a proximal end for discharging fluid, which discharged fluid is to be received in an orifice of a detector, said discharge tube having at least one wall defining an external surface and at least one wall defining an internal surface, comprising:

a tube housing for mounting at or about an orifice of a detector, said tube housing having at least one exterior surface and at least one internal wall defining a chamber having a proximal opening for positioning about said orifice of a detector and a distal opening away for said orifice of a detector, said chamber constructed and arranged to receive a discharge tube in said distal opening and projecting from said proximal opening, said chamber in communication with source of a carrier gas, said carrier gas conveyed to the proximal opening of said chamber between the external wall of said discharge tube and said internal wall of said chamber; said chamber having a wide section at said distal opening, and a narrow section towards said proximal opening, and a conical section, said conical section interposed between said narrow section and said wide section and;

tube securing means affixed to said wide section and conical section of said tube housing and engaging said discharge tube in a release mode and a securing mode, in said release mode said discharge tube is slideably engaged to allow said discharge tube to be moved within said chamber in a selected position with respect to said proximal opening of said tube housing, and in said securing mode said discharge tube is fixed, said tube securing means having sealing means for substantially closing said distal opening with said discharge tube to said carrier gas when said tube securing means is in said securing mode, and at least one of said tube housing and said tube securing means capable of securing said tube housing at or about said orifice of said detector to facilitate the alignment of said discharge tube with said orifice of said detector.

2. The apparatus of claim 1 wherein said tube securing means comprises at least one ferrule, said ferrule having an ferrule opening for receiving said discharge tube and a conical shape for cooperating with said conical section of chamber, said ferrule received in said conical section with said discharge tube in said ferrule opening to sealing engage said conical section of said chamber and said exterior surface of said discharge tube upon compression to prevent said carrier gas from exiting said chamber at said distal opening and to fix said position of said discharge tube.

3. The apparatus of claim 2 wherein at least one of said ferrule or tube housing is comprised of a compressible material.

4. The apparatus of claim 3 wherein said compressible material is selected from the group consisting of deformable metals conductive polymers, polymers and plastics and solid agglomerated forms.

5. The apparatus of claim 2 wherein said tube securing means comprises ferrule compression means.

6. The apparatus of claim 5 wherein said ferrule compression means comprises a screw having threads and said chamber at said wide opening has threads for receiving said screw to allow said screw to be secured and tightened against said ferrule.

7. The apparatus of claim 6 wherein said screw has at least one handle means for facilitating turning of the screw.

8. The apparatus of claim 1 wherein said chamber is in communication with a source of carrier gas by a carrier gas conduit.

9. The apparatus of claim 1 wherein said tube housing has a projecting conduit in communication with said chamber at said proximal opening, said projecting is conduit electro-conductive to place a charge upon one or more droplets discharged from a discharge tube and to direct said droplets bearing a charge towards said orifice.

10. The apparatus of claim 1 further comprising a discharge tube having a distal end for receiving fluid and a proximal end for discharging fluid, which discharged fluid is to be received in an orifice of a detector, said discharge tube having at least one wall defining an external surface and at least one wall defining an internal surface.

11. The apparatus of claim 1 further comprising a union assembly for receiving said distal end of said discharge tube and placing said discharge tube in communication with a source of fluid.

12. The apparatus of claim 11 wherein said source of fluid is a fused capillary.

13. The apparatus of claim 12 wherein said union assembly comprises a union housing having a union chamber for receiving said fused capillary and said discharge tube.

14. The apparatus of claim 13 wherein said union assemble further comprises capillary securing means and discharge tube securing means.

15. The apparatus of claim 14 wherein said capillary securing means comprises at least one capillary ferrule means and one capillary screw element, said capillary screw element having a capillary opening for receiving said fused capillary and said capillary ferrule means sealing engages said capillary and said union housing upon compression.

16. The apparatus of claim 14 wherein said discharge tube securing means comprises at least one tube ferrule means and one tube screw element, said tube screw element having a tube opening for receiving said discharge tube and said tube ferrule sealing engages said discharge tube and said union housing upon compression.

17. The apparatus of claim 13 wherein said union housing is electro-conductive to place a charge on ions in solution flowing through said union chamber.

18. The apparatus of claim 13 further comprising a mounting assembly, said mounting assembly affixing said tube housing in position with respect to said orifice of said detector and affixing said union assembly in position with respect to said tube housing.

19. The apparatus of claim 18 wherein said mounting assembly comprises a union holder, said union holder having union affixing means for detaching and affixing said union assembly.

20. The apparatus of claim 19 wherein said union holder has a body having a channel for receiving said union housing.

21. The apparatus of claim 19 wherein said mounting assembly has slide means for slidably positioning said union holder with respect to said tube housing.

22. The apparatus of claim 21 wherein said mounting assembly comprises a plate having slide means.

23. The apparatus of claim 22 wherein said plate and said union holder have cooperating sliding track and carriage means.

24. The apparatus of claim 23 wherein said sliding track comprises one or more grooves at least one of said grooves having one or more retaining ridges.

25. The apparatus of claim 23 wherein said carriage means comprises a carriage section of said union holder said carriage section having one or more keyed edges said keyed edges retained in said groove by said retaining ridge.

26. The apparatus of claim 24 further comprising locking means to fix the position of said union holder with respect to said tube housing.

27. The apparatus of claim 26 wherein said union holder has a locking screw and a locking screw opening, said locking screw and locking screw opening having cooperating threads, said locking screw having a release position in which said union holder slides in said one or more grooves and a locked position in which said union holder is unable to move to fix the union holder in position.

28. The apparatus of claim 1 further comprising mass spectrometer means said discharge tube discharging fluid towards an orifice of said mass spectrometer means.

29. A method of making a fluid discharge apparatus comprising the steps:

a.) providing an apparatus, for holding a discharge tube having a distal end for receiving fluid and a proximal end for discharging fluid, which discharged fluid is to be received in an orifice of a detector, said discharge tube having at least one wall defining an external surface and at least one wall defining an internal surface, said apparatus having a tube housing for mounting at or about an orifice of a detector, said tube housing having at least one exterior surface and at least one internal wall defining a chamber having a proximal opening for positioning about said orifice of a detector and a distal opening away for said orifice of a detector, said chamber constructed and arranged to receive a discharge tube in said distal opening and projecting from said proximal opening, said chamber in communication with source of a carrier gas, said carrier gas conveyed to the proximal opening of said chamber between the external wall of said discharge tube and said internal wall of said chamber; said chamber having a wide section at said distal opening, and a narrow section towards said proximal opening, and a conical section, said conical section interposed between said narrow section and said wide section and;

tube securing means affixed to said wide section and conical section of said tube housing and engaging said discharge tube in a release mode and a securing mode, in said release mode said discharge tube is slideably engaged to allow said discharge tube to be moved within said chamber in a selected position with respect to said proximal opening of said tube housing, and in said securing mode said discharge tube is fixed, said tube securing means having sealing means for substantially closing said distal opening with said discharge tube to said carrier gas when said tube securing means is in said securing mode, and at least one of said tube housing and said tube securing means capable of securing said tube housing at or about said orifice of said detector to facilitate the alignment of said discharge tube with said orifice of said detector; and, inserting a discharge tube in said distal opening of said tube housing through said chamber and projecting from said proximal opening;

securing said discharge tube with securing means to affix said discharge tube and seal said distal opening.

30. The method of claim 29 wherein said tube securing means comprises at least one ferrule, said ferrule having an ferrule opening for receiving said discharge tube and a conical shape for cooperating with said conical section of chamber, said ferrule received in said conical section with said discharge tube in said ferrule opening to sealing engage said conical section of said chamber and said exterior surface of said discharge tube upon compression to prevent said carrier gas from exiting said chamber at said distal opening and to fix said position of said discharge tube, said method further comprising the step of fitting said ferrule to said discharge tube.

31. The method of claim 30 wherein at least one of said ferrule or tube housing is comprised of a compressible material.

32. The method of claim 31 wherein said compressible material is selected from the group consisting of deformable metals, conductive polymers, polymers and plastics and solid agglomerated forms.

33. The method of claim 30 wherein said tube securing means comprises ferrule compression means and said method further comprises the step of compressing said ferrule with ferrule compression means.

34. The method of claim 33 wherein said ferrule compression means comprises a screw having threads and said chamber at said wide opening has threads for receiving said screw to allow said screw to be secured and tightened against said ferrule.

35. The method of claim 34 wherein said screw has at least one handle means for facilitating turning of the screw, and said method comprises the step of moving said handle means.

36. The method of claim 29 wherein said chamber is in communication with a source of carrier gas by a carrier gas conduit.

37. The method of claim 29 wherein said tube housing has a projecting conduit at said proximal opening, said projecting conduit is electro-conductive to place a charge upon one or more droplets discharged from a discharge tube and to direct said droplets bearing a charge towards said orifice and said discharge tube positioned with respect to said conduit.

38. The method of claim 29 wherein said apparatus further comprising a union assembly for receiving said distal end of said discharge tube and placing said discharge tube in communication with a source of fluid, said method comprising the step of placing said distal end of said discharge tube in communication with said union assembly.

39. The method of claim 38 wherein said source of fluid is a fused capillary.

40. The method of claim 39 wherein said union assembly comprises a union housing having a union chamber for receiving said fused capillary and said discharge tube and said method comprises the step of fitting said discharge tube and said fused capillary in said union housing.

41. The method of claim 40 wherein said union assembly further comprises capillary securing means and discharge tube securing means and said method comprises the step of securing said discharge tube and said capillary fitted in said union housing with said securing means.

42. The method of claim 41 wherein said capillary securing means comprises at least one capillary ferrule means and one capillary screw element, said capillary screw element having a capillary opening for receiving said fused capillary and said capillary ferrule means sealing engages said capillary and said union housing upon compression, said method comprising the step of fitting said capillary ferrule means and said capillary screw element to said capillary and compressing said capillary ferrule means with said capillary screw element to secure said fused capillary to said union.

43. The method of claim 41 wherein said discharge tube securing means comprises at least one tube ferrule means and one tube screw element, said tube screw element having a tube opening for receiving said discharge tube and said tube ferrule sealing engages said discharge tube and said union housing upon compression, said method comprising the step of fitting said tube ferrule means and said tubed screw element to said discharge tube and compressing said tube ferrule means with said tube screw element to secure said discharge tube to said union.

44. The method of claim 40 wherein said union housing is electro-conductive to place a charge on ions in solution flowing through said union chamber.

45. The method of claim 41 wherein said apparatus further comprises a mounting assembly, said mounting assembly affixing said tube housing in position with respect to said orifice of said detector and affixing said union assembly in position with respect to said tube housing.

46. The method of claim 45 wherein said mounting assembly comprises a union holder, said union holder having union affixing means for detaching and affixing said union assembly.

47. The method of claim 46 wherein said union holder has a body having a channel for receiving said union housing.

48. The method of claim 47 wherein said mounting assembly has slide means for slidably positioning said union holder with respect to said tube housing said method comprising the step of sliding said union holder in position with respect to said tube housing with said discharge tube abutting said fused capillary.

49. The method of claim 48 wherein said mounting assembly comprises a plate having slide means.

50. The method of claim 49 wherein said plate and said union holder have cooperating sliding track and carriage means.

51. The method of claim 50 wherein said sliding track comprises one or more grooves and at least one of said grooves having one or more retaining ridges to slideably hold said carriage means as said carriage means is positioned with respect to said tube housing.

52. The method of claim 51 wherein said carriage means comprises a carriage section of said union holder said carriage section having one or more keyed edges said keyed edges retained in said groove by said retaining ridge to allow said carriage means to be slideably held in said retaining groove of said plate to allow positioning of said union holder with respect to said tube housing.

53. The method of claim 52 wherein said apparatus further comprising locking means to fix the position of said union holder with respect to said tube housing said method comprising the step of using locking means to fix the position of said union holder.

54. The method of claim 53 wherein said locking means comprises a locking screw and a locking screw opening in said union housing, said locking screw and locking screw opening having cooperating threads, said locking screw having a release position in which said union holder slides in said one or more grooves and a locked position in which said union holder is unable to move to fix the union holder in position, said method further comprising the step of placing said locking screw in one of said positions.

55. The method of claim 29 wherein said apparatus further comprising mass spectrometer means said discharge tube discharging fluid towards an orifice of said mass spectrometer means.

56. An apparatus for performing chromatography and mass spectrometry comprising chromatography apparatus, mass spectrometry apparatus and a interface,
    said chromatograph apparatus having a exit conduit comprising a capillary,
    said mass spectrometry apparatus having a orifice,
    said interface interposed between said chromatography apparatus and said mass spectrometry apparatus, said interface having a discharge tube having a distal end for receiving fluid from said capillary and a proximal end for discharging fluid, which discharged fluid is to be received in an orifice of said mass spectrometer, said discharge tube having at least one wall defining an external surface and at least one wall defining an internal surface, comprising:
    a tube housing for mounting at or about said orifice, said tube housing having at least one exterior surface and at least one internal wall defining a chamber having a proximal opening for positioning about said orifice and a distal opening away for said orifice, said chamber constructed and arranged to receive said discharge tube in said distal opening and projecting from said proximal opening, said chamber in communication with source of a carrier gas, said carrier gas conveyed to the proximal opening of said chamber between the external wall of said discharge tube and said internal wall of said chamber; said chamber having a wide section at said distal opening, and a narrow section towards said proximal opening, and a conical section, said conical section interposed between said narrow section and said wide section and;
    tube securing means affixed to said wide section and conical section of said tube housing and engaging said discharge tube in a release mode and a securing mode, in said release mode said discharge tube is slideably engaged to allow said discharge tube to be moved within said chamber in a selected position with respect to said proximal opening of said tube housing, and in said securing mode said discharge tube is fixed, said tube securing means having sealing means for substantially closing said distal opening with said discharge tube to said carrier gas when said tube securing means is in said securing mode, and at least one of said tube housing and said tube securing means capable of securing said tube housing at or about said orifice of said detector to facilitate the alignment of said discharge tube with said orifice.

* * * * *